(12) United States Patent
Sanders

(10) Patent No.: US 7,702,189 B2
(45) Date of Patent: Apr. 20, 2010

(54) FIBER OPTIC CHEMICAL SENSOR

(75) Inventor: Glen A. Sanders, Scottsdale, AZ (US)

(73) Assignee: Honeywell International Inc., Morristown, NJ (US)

( * ) Notice: Subject to any disclaimer, the term of this patent is extended or adjusted under 35 U.S.C. 154(b) by 294 days.

(21) Appl. No.: 11/757,904

(22) Filed: Jun. 4, 2007

(65) Prior Publication Data
US 2009/0067775 A1    Mar. 12, 2009

(51) Int. Cl.
*G02B 6/00* (2006.01)
(52) U.S. Cl. .......................................... 385/12; 385/13
(58) Field of Classification Search ................... 385/12, 385/13
See application file for complete search history.

(56) References Cited

U.S. PATENT DOCUMENTS

| | | | | |
|---|---|---|---|---|
| 4,834,496 A | * | 5/1989 | Blyler et al. .................. | 385/12 |
| 4,846,548 A | * | 7/1989 | Klainer ........................ | 385/12 |
| 5,337,376 A | * | 8/1994 | Ravetti et al. ................. | 385/12 |
| 5,982,959 A | * | 11/1999 | Hopenfeld .................... | 385/12 |
| 6,842,548 B2 | * | 1/2005 | Loock et al. .................. | 385/15 |
| 7,483,144 B2 | * | 1/2009 | Sanders ....................... | 356/480 |
| 7,518,730 B2 | * | 4/2009 | Yates et al. ................... | 356/480 |
| 2004/0263856 A1 | * | 12/2004 | Willig et al. ................. | 356/460 |
| 2006/0227331 A1 | * | 10/2006 | Vollmer et al. ............... | 356/483 |
| 2008/0030741 A1 | | 2/2008 | Digonnet et al. | |

* cited by examiner

*Primary Examiner*—Daniel Petkovsek
(74) *Attorney, Agent, or Firm*—Fogg & Powers LLC

(57) ABSTRACT

Optical systems for sensing chemicals. An example system includes a light source, a light sensor, a processing device in signal communication with the light source and the light sensor, and a fiber optic cable that receives light from the light source and delivers light to the light sensor. The fiber optic cable includes a cladding material that is permeable to a predefined substance and an optical fiber core surrounded by the cladding material. The optical fiber core is a single mode optical fiber having a diameter greater than 30 μm. The optical fiber core includes a hollow center having a diameter between 1-50 μm. The optical fiber core includes a plurality of lengthwise holes positioned to provide single mode light propagation properties. The plurality of lengthwise holes have a diameter between 0.2-4 μm.

15 Claims, 4 Drawing Sheets

FIBER OPTIC CHEMICAL SENSOR

BACKGROUND OF THE INVENTION

Optical fiber consists of transparent material such as glass or plastic. Most optical fiber is fused silica and most plastic fiber is polymethylmethacrylate (PMMA). All optical fiber consists of a core and cladding of which the core has higher refractive index than the cladding. The fiber structure guides light by the process of total internal reflection (TIR). In silica fibers the core is usually established through doping with Germanium. PMMA uses a Fluorine polymer coating as the cladding. Fibers fall into two basic types, single mode or multimode. In single-mode fibers the core is very small, 5 to 10 microns in diameter, for instance. Multimode fibers have cores of 50 to several thousand microns and very small cladding (in the order of tens of microns). Single-mode fibers have a large cladding (usually more than 50 microns) making the fiber diameter generally 125 microns (FIG. 1). The purpose of the large cladding in single-mode fibers is to protect and contain the evanescent field of the single-mode which extends into the cladding for a few microns and can contain more than 10 percent of the optical energy normally thought of as traveling only through the core. Another importance of this larger diameter cladding is so that the fibers can be handled without breaking. However, with regard to fiber optics used for chemical sensing, the cladding must be permeable to the substance being sensed. Thus, a small diameter fiber surrounded by a thick cladding is not practical for chemical fiber optic sensors.

Large core fibers experience a relatively large number of spatial modes, possibly in the hundreds. Light traveling in different spatial modes travels at different speeds. Due to unavoidable perturbations, light can and does couple from one mode to another (so-called "mode mixing"). Mode mixing, and different light speeds between various modes causes noise and uncertainty in light detection systems and causes pulse spreading in communication systems. For this reason, single-spatial mode (single mode) fibers are used in many communications and sensing systems. One advantage, however, of multi-mode fiber is its large core area has a diameter with sufficient structural integrity and can be coated with a chemically sensitive polymer which can function as its cladding. In fact, chemically sensitive multi-mode fibers have been realized by embedding chemical indicators in a porous polymer coating which functions as the fiber cladding. Light traveling along the fiber core with its evanescent field extending into the cladding will experience higher loss when the indicator is triggered by the presence of a specific gaseous chemical.

Because the core size of a standard single-mode fiber is typically 10 µm, it is too fragile when cladded with porous indicator-embedded polymers that have been proven for use on multimode fibers. This is because the glass is thin, and polymer is not sufficiently rigid to maintain structural integrity of the fiber. FIG. 2 shows an optical fiber for use in chemical sensing that includes a glass core and a cladding material. Although the optical fiber of FIG. 2 is durable, it is a multi-mode fiber Resonators have been implemented in chemical sensors to circulate light around an optical fiber loop for multiple passes. A periodic series of resonance lineshapes is produced, each having a peak centered about a resonance frequency under normal conditions, and the resonance lineshape has a finesse associated therewith. The frequency-periodicity of frequency separation between resonance frequencies of the same mode is the free spectral range of the resonator. As used herein, the term "finesse" refers to a relationship (e.g., sharpness) based on a ratio of the free-spectral range to the linewidth of an individual resonance lineshape. The linewidth of the resonance lineshape is a frequency width at half of the maximum peak value of the resonance lineshape. The finesse additionally relates to the number of times the light recirculates within the optical loop with reproducibility, and thus is inherently related to the round-trip loss of the resonator. Higher losses generally result in lower finesses. It is generally difficult to couple light into a multi-mode optical fiber and maintain the light in a single spatial mode that reproduces itself for multiple circulations through the resonator. For example, perturbations (e.g., imperfections, geometrical distortions, etc.) along the length of the optical fiber typically decrease the round-trip reproducibility of the single fiber spatial mode within a multi-mode fiber, and thus decrease the finesse. Other spatial mode resonances can also be excited which typically cause errors in the intended measurement. In the latter case, a complex structure of resonances, which may be based on a single stable resonance, may be observed that create instabilities and errors in the measurement. Each spatial mode may be associated with two polarization modes, which doubles the number of resonances in the spectrum.

A single mode optical fiber may be used to significantly improve the resonance characteristics of the resonator by assuring that a single spatial mode of the fiber supports the resonance mode of the resonator. For example, this single spatial mode is the sole resonating mode provided that one polarization state is resonating within the resonator. Instabilities created by power sharing between several spatial modes of the fiber and errors resulting from the presence of several resonator modes are thus substantially eliminated. Measurements of the finesse, the linewidth of the resonance, and the free spectral range are typically unique since these relate to the loss and pathlength for light traveling within a single spatial mode of the fiber and for a single resonance lineshape. To make a chemically sensitive fiber, the light should interact with the polymer. Placing a permeable, chemically sensitive polymer cladding directly on the core of a typical single mode fiber is generally impractical because the core is too small, as discussed above. Adding an intermediate glass cladding between the core and a polymer coating would tend to interfere with sensing.

SUMMARY OF THE INVENTION

The present invention provides systems for sensing chemicals. An example system includes a light source, a light sensor, a processing device in signal communication with the light source and the light sensor, and an optical fiber arranged within a resonator that receives light from the light source and delivers light to the light sensor. The optical fiber includes a cladding material that is permeable to a predefined substance and has indicators embedded within that make its optical properties (attenuation and refractive index) sensitive to a target substance, and an optical fiber core that is surrounded by the cladding material. A single mode optical fiber is provided with a glass core size having a diameter greater than 30 µm.

In one aspect of the invention, the optical fiber core includes a hollow center having a diameter between 1-50 µm.

In another aspect of the invention, the optical fiber core includes a plurality of lengthwise holes positioned to provide single mode light propagation properties. The plurality of lengthwise holes have a diameter between 0.2-4 µm.

In still another aspect of the invention, the optical fiber core includes a hollow center and a plurality of lengthwise holes having a diameter between 0.2-4 µm.

BRIEF DESCRIPTION OF THE DRAWINGS

Preferred and alternative embodiments of the present invention are described in detail below with reference to the following drawings.

DETAILED DESCRIPTION OF THE PREFERRED EMBODIMENT

Figure 1:
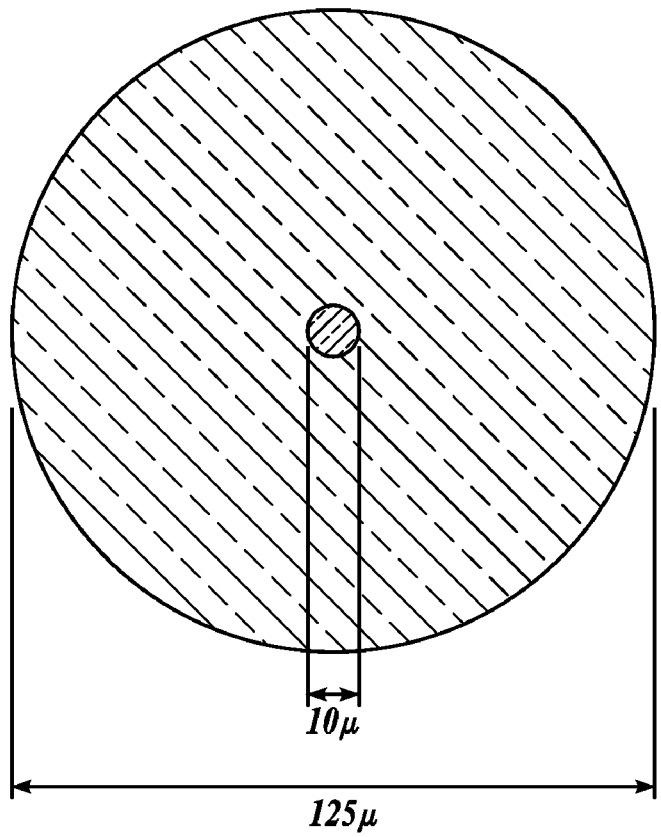
FIGS. 1 and 2 illustrate cross-sectional views of fiber optic cable formed in accordance with embodiments of the prior art.
Figure 2:
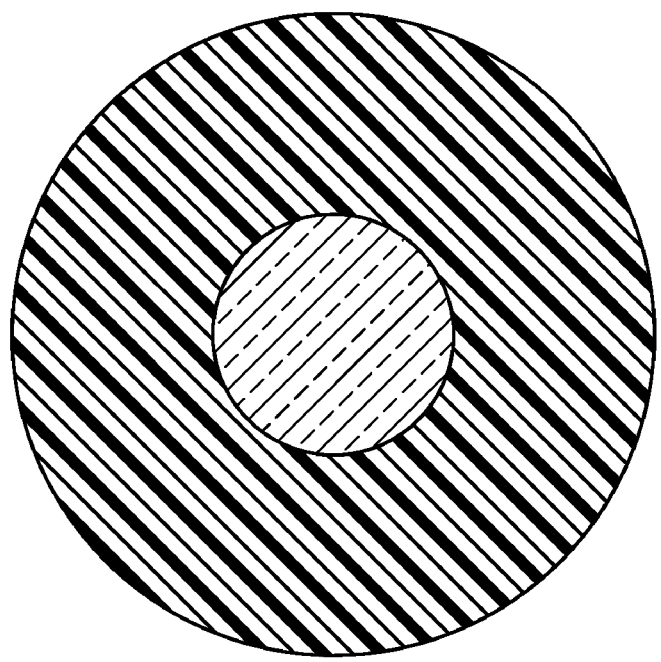
Figure 3:
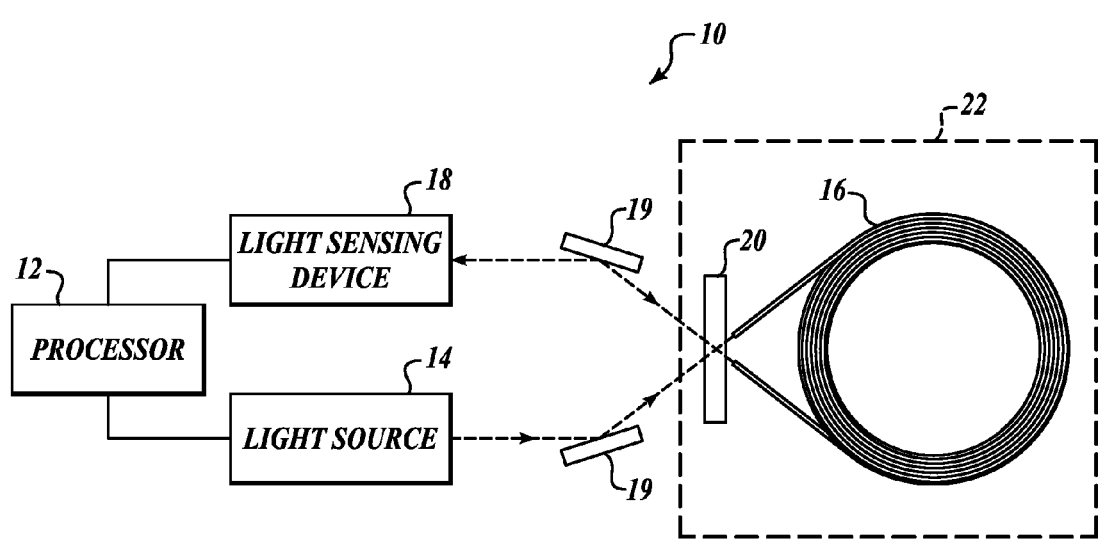
FIGS. 3-6 illustrate cross-sectional views of fiber optic cables formed in accordance with embodiments of the present invention.

FIG. 3 illustrates a chemical sensor system 10 formed in accordance with an embodiment of the present invention. The system 10 includes a processor 12, a light source 14, a loop 16 of a cladded optical fiber, a partially transmitting mirror 20, a light sensing device 18, and various optical components 19. The combination of the partially transmitting mirror 20 and the fiber loop 16 form an optical resonator 22. The processor 12 controls the light source 14 to produce a frequency modulated (or "tuned" or "scanned") laser light signal that is sent to the optical resonator 22 and received by the light sensing device 18, via the optical components 19.

When an input light beam (e.g., from a light source) is supplied to the resonator 22 and the input light beam is tuned through the region of the resonance frequency of the resonator 22 in one direction (e.g., a clockwise or a counter-clockwise direction of the optical fiber coil in the case of a ring resonator), a resonance lineshape is produced in the region of the resonance frequency, which is sensed by the light circulating through the resonator 22. Absent the agent (target substance) to be detected from the environment, the resonance lineshape has a narrow profile (high finesse), corresponding to a low round-trip energy loss of the light circulating in the resonator 22. In this case, a chemical indicator is embedded in the cladding of the fiber loop 16 and is optically transparent. In the presence of the chemical agent, the chemical indicator embedded in the cladding reacts with the agent (target substance), causing its optical properties, such as attenuation or refractive index to change. In the case of its attenuation changing, the roundtrip loss of the resonator 22 increases causing a reduction in its finesse, or a broading of its resonance profile. The sensor processing electronics (the processor 12) determine the change in resonance characteristics such as finesse or free spectral range as the laser frequency is scanned over the resonance of the resonator 22 and the light is received at the photodetector (the light sensing device 18). The light sensing device 18 receives light outputted from the fiber resonator 22 via the optical components 19 and sends a light sensing signal to the processor 12 for analysis.

In some applications such as for unmanned autonomous vehicles for chemical sensing, a high sensitivity, very small sized sensor is quite attractive. It should be noted that this invention has advantages for such applications. For instance, in an exemplary embodiment, most of the sensor 10 is constructed on a silicon-based micro-optical bench that integrates electronics (e.g., the processor 12) and optics (for example the light source 14, the light sensing device 18, the optical elements 19 and 20) and provides an efficient and expedient interface between the optics electronics and fiber. The ends of the fiber may be placed in vee-grooves and aligned to receive and transmit light to the mirror 20, located on the optical bench. Miniature optical components having a feature size of as little as 10 microns, such as mirror reflectors 19, and a recirculator 20, may be mounted on silicon surfaces to eliminate large bulk optics, even though the light wave may be traveling in free space. Some of these optical functions may also be embedded in waveguides residing in the silicon material. In this exemplary embodiment, the light source 14 and related frequency tuning components and the light sensing device 18 may also be mounted on the optical bench. The use of these techniques allows the fabrication of optics in or on a silicon platform and thus integrated with the electronics. The light source itself may be a compound structure, on which several components may be mounted, or formed on the micro-optical bench. For instance, it may be an external cavity laser diode, where the laser diode is placed between two reflective surfaces, which are either formed or placed on the substrate. There may also be frequency selective intra-cavity elements formed or placed within the laser cavity to make it a single frequency laser, such as a grating or an etalon. There may also be elements included with laser source 14 that are mounted or formed external to the laser cavity that are used to shape or collimate the laser beam, such as lenses. It is also noted that the partially transmitting mirror, or the recirculating device 20, may be replaced by a fiber optic coupler in some instances.

The fiber loop 16 includes turns of a single mode, flexible and robustly-cladded optical fiber. The fiber loop 16 allows for single-mode polarized light delivery that is strong enough to be flexible without being fragile. Examples of optical fibers for use as the fiber loop 16 are described below with regards to FIGS. 4-6.

Figure 4:
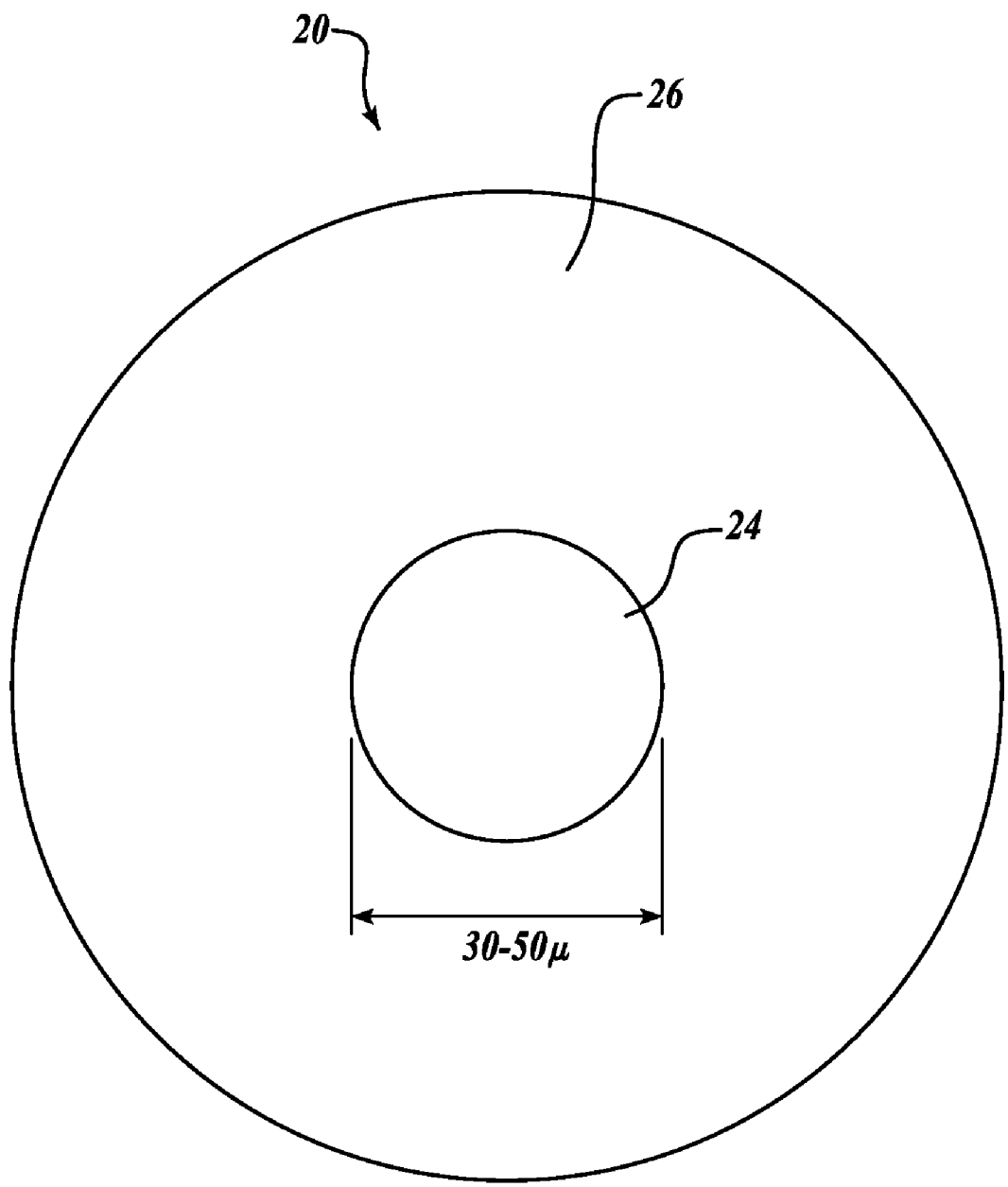

FIG. 4 illustrates a cross-sectional view of a first embodiment of a fiber optic cable 20 that provides single-mode delivery of light generated by the light source 14. The cable 20 includes two components, a glass core 24 having a first index of refraction $n_1$ and a cladding material 26 that surrounds the glass core 24. The cladding material 26 is preferably a polymer having an index of refraction $n_2$ that is lower than $n_1$. Typically in the prior art, these fibers are multimode because of the large core diameter and the large index difference. However, in this invention, the cladding material 26 is preferably a polymer having an index of refraction $n_2$ that is just very slightly lower than $n_1$. This enables single mode operation, and a diameter of the glass core 24 that is greater than a threshold size that would provide for mechanical stability greater than a predefined length, such as a few meters or a few tens of meters. For example, as shown in FIG. 4, the diameter of the glass core 24 is approximately 30 µm to 100 µm. In this method, the polymer's (cladding's) index of refraction is increased by adding dopants, or the polymer is chosen to have an index just below that of fused silica, so the index difference with the core is very small, yet the index of the polymer is still lower than that of the core.

An example of the polymer is an acrylate with dopants and an indicator embedded within. In another embodiment, the core can also be doped to lower its index of refraction by the use of a dopant such as fluorine to partially accomplish the objective of a lower refractive index difference with the polymer.

Figure 5:
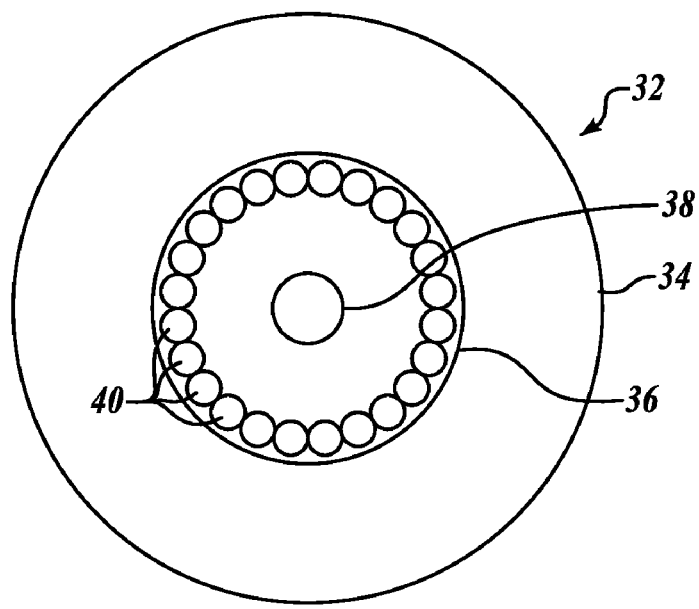

FIG. 5 shows an alternative to the fiber arrangement in FIG. 4. FIG. 5 illustrates another single-mode fiber optic cable 32. The cable 32 includes a cladding material 34 that surrounds a glass core 36. The glass core 36 includes a hole 38 located in the center of the glass core 36 and a plurality of smaller holes 40 that surround the center hole 38 that are positioned near to the exterior edge of the glass core 36. The optical fiber can be made to be single mode. The hole pattern structures are consistent with those made for microstructured fibers, such as those produced for glass fibers by Crystal Fibre A/S of Denmark. The resulting fundamental mode of the fiber is a "hoop mode" whose intensity distribution is circularly symmetric and is peaked in between the outer radius of hole 38 and the holes 40. The evanescent field extends into the indicator-embedded, semiporous polymer cladding material 34, making the fiber sensitive to the indicator when triggered by a chemical agent. Using this structure, the light is contained in a hoop mode, and glass-member diameters of 30 μm may be obtained by sizing the holes, and the distances between them, appropriately. It should be noted that (while not shown in FIG. 5) other designs with a ring of holes similar to those of the ring of holes 40, around central hole 38, or more concentric rings of holes inside the ring of holes 40 to achieve the desired results.

Figure 6:
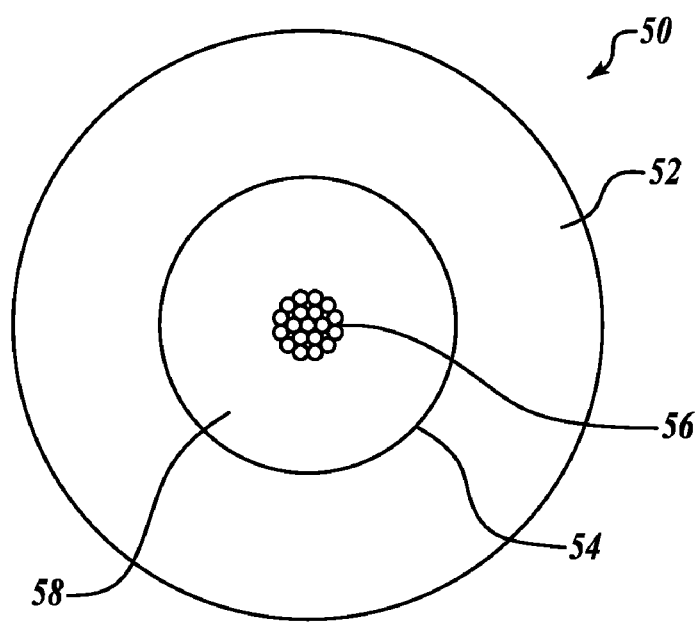

FIG. 6 illustrates another fiber optic cable 50 that includes a polymer or other type of cladding material 52 that surrounds a glass core 54. The glass core 54 includes a series of holes 56 and a solid region 58 around them. The holes 56 in the center assure that the light mode does not propagate in the center, and the cladding confines the light to be inside the region 58. Again, the light is propagating in a hoop mode. By adjusting the cladding index of refraction and the hole sizes and spacing, higher spatial modes may be attenuated, the glass core 54 may be made large enough (~30 microns) to be robust, and the evanescent field may be tailored to extend into the cladding of choice.

The size of the center hole 38 is in the range of approximately 1-50 μm. The size of the holes 40, 56, are in the range of approximately 0.2-4 μm.

In another embodiment, the glass cores 24, 36, 54 may be doped in order to decrease its index of refraction $n_1$.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

The invention claimed is:

1. A chemical sensor comprising:
an optical resonator comprising a cable, the cable comprising:
an optical fiber comprising:
a cladding material being permeable to a predefined chemical substance and having a chemical indicator embedded therein, wherein the optical properties of the cladding material change when exposed to the predefined chemical substance; and
an optical fiber core surrounded by the cladding material, the optical fiber core having a diameter greater than about 30 μm;
wherein the optical fiber is a single mode optical fiber, and the chemical indicator reacts with the predefined chemical substance to change the optical properties of the cladding material.

2. The sensor of claim 1, wherein the optical fiber core includes a hollow center having a diameter between about 1-50 μm.

3. The sensor of claim 1, wherein the optical fiber core includes a plurality of lengthwise holes positioned to provide single mode light propagation properties.

4. The sensor of claim 3, wherein the plurality of lengthwise holes have a diameter between about 0.2-4 μm.

5. The sensor of claim 1, wherein the optical fiber core includes a hollow center having a diameter between about 1-50 μm and a plurality of lengthwise holes having a diameter between about 0.2-4 μm, the hollow center and the plurality of lengthwise holes being positioned to provide single mode light propagation properties.

6. A chemical sensor comprising:
a laser light source;
a light sensor;
a processing device in signal communication with the light source and the light sensor; and
an optical resonator comprising:
an optical fiber comprising:
a cladding material being permeable to a predefined chemical substance and having a chemical indicator embedded therein, wherein the optical properties of the cladding material change when exposed to the predefined chemical substance; and
an optical fiber core surrounded by the cladding material, the optical fiber core having a diameter greater than about 30 μm;
wherein the optical fiber is a single mode optical fiber, and the chemical indicator reacts with the predefined chemical substance to change the optical properties of the cladding material; and
a device for circulating light within the optical fiber core;
wherein said optical resonator is configured to receive light from the laser light source and to deliver light to the light sensor.

7. The sensor of claim 6, wherein the optical fiber core includes a hollow center having a diameter between about 1-50 μm.

8. The sensor of claim 6, wherein the optical fiber core includes a plurality of lengthwise holes positioned to provide single mode light propagation properties.

9. The sensor of claim 8, wherein the plurality of lengthwise holes have a diameter between about 0.2-4 μm.

10. The sensor of claim 6, wherein the optical fiber core includes a hollow center having a diameter between about 1-50 μm and a plurality of lengthwise holes having a diameter between about 0.2-4 μm, the hollow center and the plurality of lengthwise holes being positioned to provide single mode light propagation properties.

11. The sensor of claim 6, wherein the cladding material has an average index of refraction that is sufficiently below the index of refraction of the core in order to provide single mode operation of the optical fiber.

12. The sensor of claim 6, wherein the laser output of the laser light source is swept across a predefined frequency range, and wherein the processing device determines changes in at least one of the finesse or the free spectral range of the resonator as an indication of the presence of the chemical substance based on a signal from the light sensor.

13. The sensor of claim 6, further comprising a common substrate and optical components configured to couple light from said laser light source to said resonator and from said resonator to said light sensor, wherein said laser light source, said light sensor, and said optical components are at least one of attached to, mounted on, or formed on said common substrate.

14. The sensor of claim 13, wherein said device for circulating light is at least one of attached, formed or mounted on said common substrate.

15. The sensor of claim 13, wherein said processing device is at least one of attached, formed or integrated on said common substrate.

* * * * *